United States Patent [19]

Evans

[11] Patent Number: 4,518,383
[45] Date of Patent: May 21, 1985

[54] INSTRUMENT AND METHOD FOR EPIDURAL AND SPINAL ANAESTHESIA

[76] Inventor: John M. Evans, Nuffield Department of Anaesthetics, The Radcliffe Infirmary, Oxford OX2 6HE, England

[21] Appl. No.: 519,788

[22] Filed: Aug. 2, 1983

[30] Foreign Application Priority Data

Aug. 6, 1982 [GB] United Kingdom ............... 8222799

[51] Int. Cl.³ ............................................. A61M 5/00
[52] U.S. Cl. .................................. 604/51; 604/164; 604/272
[58] Field of Search ................... 604/51, 158–163, 604/272

[56] References Cited

U.S. PATENT DOCUMENTS 4,202,332 5/1980 Tersteegen et al. ............ 604/164
4,308,875 1/1982 Young ............................ 604/164 X

FOREIGN PATENT DOCUMENTS 2405918 8/1975 Fed. Rep. of Germany ...... 604/272
690847 9/1930 France ........................... 604/272
1536352 8/1968 France ........................... 604/158

Primary Examiner—Stephen C. Pellegrino
Attorney, Agent, or Firm—Pollock, Vande Sande and Priddy

[57] ABSTRACT

An instrument for epidural and spinal anaesthesia has outer and inner needle assemblies. The outer assembly has a hollow needle the forward end of which is bent at an angle of about 20° and has an inclined, pointed tip that makes an angle of about 10° with the axis of the instrument. The needle has a hub at its rear end which is provided with a keyway on its outer surface. The inner assembly has a hollow needle that extends within the needle of the outer assembly and projects from its forward end. The inner needle also has an inclined, pointed tip that makes an angle of about 30° with the axis of the instrument. The tips of the two needles lie in planes substantially at right angles to each other. At its rear end, the inner assembly has a transparent hub with a key that locates in the keyway so as to ensure correct orientation of the two assemblies.

12 Claims, 11 Drawing Figures

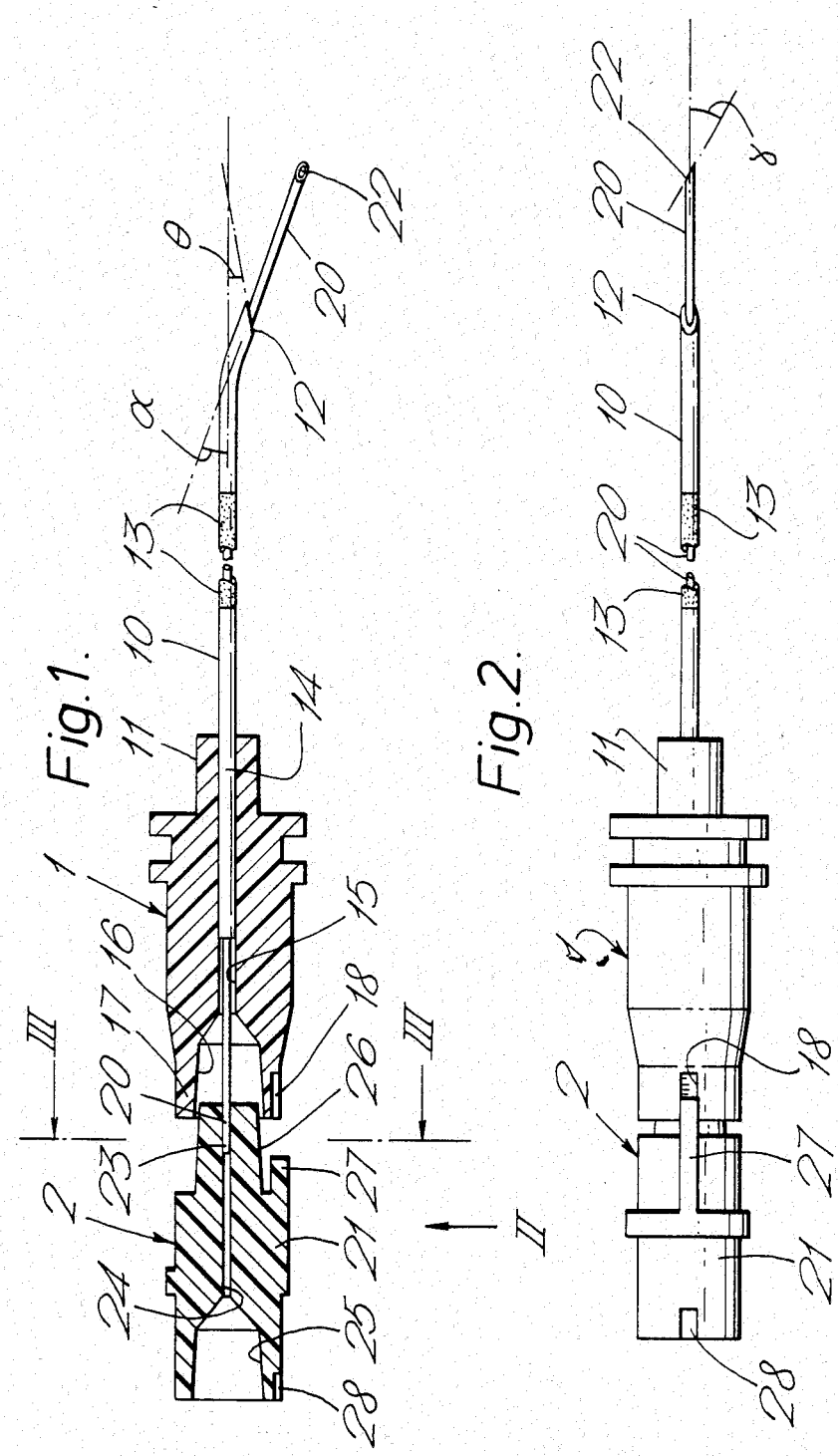

INSTRUMENT AND METHOD FOR EPIDURAL AND SPINAL ANAESTHESIA

BACKGROUND OF THE INVENTION

This invention relates to medico-surgical instruments.

The invention is more particularly concerned with instruments for use in epidural and spinal anaesthesia.

Spinal anaesthesia relies on the administration of small quantities of an anaesthetic agent into the dura, or subarachnoid. This is a relatively simple procedure and has the further advantages of being quick-acting and producing good muscle relaxation. The disadvantages, however, of this procedure are that it is only effective for short periods and that penetration of the dura can produce a severe headache in the patient.

It is common practice now to use spinal anaesthesia in conjunction with epidural anaesthesia which, though being slower to act, and less effective at muscle relaxation, has the advantage of being easier to prolong anaesthesia by the repeated or continual administration of an anaesthetic agent via an epidural catheter. Thus, a spinal anaesthetic is administered initially which is followed by continual epidural anaesthesia for the desired period.

Usually, the spinal and epidural insertions are made at separate sites but it has been found to be advantageous to carry out both procedures at the same site since this reduces discomfort of the patient and shortens the time taken to administer the anaesthetic. It has been proposed to use a Tuohy needle to locate the epidural space in the usual way, and then to insert a spinal needle through the Tuohy needle so that it emerges from the tip of the Tuohy needle and penetrates the dura. An anaesthetic agent can then be administered through the spinal needle. The spinal needle is subsequently withdrawn, leaving the Tuohy needle in position for use in introduction of an epidural catheter in the usual way.

During epidural and spinal anaesthesia, in order to reduce discomfort of the patient, it is important that the sharp, inclined tips of both the Tuohy and spinal needles are aligned with the "grain" of the tissues through which they are inserted so that cutting of the tissue is minimized and healing facilitated.

BRIEF SUMMARY OF THE INVENTION

It is an object of the present invention to provide an instrument that will ensure correct orientation of the needles with respect to one another during placement.

According to one aspect of the present invention there is provided a medico-surgical instrument for use in epidural and spinal anaesthesia, including an outer hollow needle assembly and an inner hollow needle assembly each said assembly having an inclined, pointed tip, wherein said inner needle assembly is slidable coaxially within said outer needle assembly, the rear ends of said inner and outer needle assemblies being provided with cooperating engagement members that are locateable with one another to define a predetermined relative angular orientation between the inner and outer needle assemblies, wherein said inner needle assembly is arranged to project from the forward end of said outer needle assembly when said engagement members are located with one another.

The outer needle assembly may have a forward end that is bent away from the longitudinal axis of the instrument and thus may be at an angle $\alpha$ of substantially 20°. The engagement members may be provided by a key and keyway which may be provided on the outer surface of the inner and outer needle assemblies. The pointed tip of the outer needle assembly may make an angle $\theta$ of substantially 10° with the longitudinal axis of the instrument, and the pointed tip of the inner assembly may make an angle $\gamma$ of about 30° with the longitudinal axis of the instrument. The pointed tip of the outer needle assembly may lie in a plane substantially at right angles to the pointed tip of the inner needle assembly.

An instrument in accordance with the present invention will now be described, by way of example, with reference to the accompanying drawings:

BRIEF DESCRIPTION OF THE DRAWINGS

FIG. 1 is a sectional side elevation along the instrument;

FIG. 2 is a view from below, in the direction of arrow II (FIG. 1), of the instrument;

DETAILED DESCRIPTION

Figure 3:
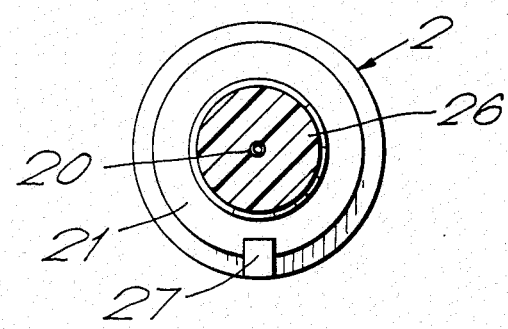
FIG. 3 is a cross sectional view of the instrument taken on line III—III of FIG. 1.

With reference to FIGS. 1 to 3, the instrument comprises an outer and inner needle assembly 1 and 2 which extend coaxially of one another. The outer needle assembly 1 has a standard metal Tuohy needle 10 which is joined at its rear end to a hub 11 of plastics material. The outer needle 10 is hollow and projects about 80 mm forwardly of the hub 11. The forward 5 mm or so of the needle 10 is bent downwardly at an angle $\alpha$ of about 20°, the end 12 of the outer needle being cut such that it makes an angle $\theta$ of about 10° with the axis of the major part of the needle. This inclined end 12 of the needle provides it with a sharp point that readily pierces body tissue.

The outer needle 10 has three marked section 13 equally spaced along its length; this enables the user to determine the extent of penetration of the tip of the needle.

At its rear end 14, the outer needle 10 extends within the hub 11 where it is secured, such as, by molding the hub around the needle. The bore through the needle 10 opens into an axially-aligned bore 15 through the hub 11 of the same diameter as the needle bore. The rear end of the bore is enlarged and tapered to provide a female Luer opening 16 for use in receiving the inner needle assembly 2. At the rear end 17 of the hub 11 an axially-extending slot or keyway 18 is formed in the outer surface of the hub, on that side of the hub to which the forward end 12 of the needle 10 is inclined.

The inner needle assembly 2 similarly comprises a hollow metal needle 20 joined at its rear end with a hub 21 of plastics material. The inner needle 20 is smaller in diameter than the outer Tuohy needle 10 and, in its natural state is straight along its entire length. The forward end 22 of the inner needle 20 is inclined at an angle $\gamma$ of about 30° to its length giving it a sharply pointed tip. The inner needle 20 is longer than the outer needle 10 such that, when both assemblies 1 and 2 are joined, the inner needle projects by about 10 mm from the forward end 12 of the outer needle. At its rear end 23, the inner needle 20 extends a short distance within the hub 21 in which it is joined. The hub 21 is of a transparent plastics material the purpose of which will become apparent later.

The bore through the inner needle 20 opens at its rear end 23 into a bore 24 of similar diameter which extends axially through the hub 21. Towards the rear end of the hub 21 the bore 24 is enlarged and tapered to provide a female Luer opening 25. The external surface of the hub 21 is of generally cylindrical shape, the forward end 26 having a Luer taper that is dimensioned to fit within the Luer-tapered opening 16 in the other hub 11. A short peg or key 27 of rectangular section is provided along the lower side of the hub 21, as viewed in FIG. 1. The peg 27 extends axially of the hub 21, being spaced outwardly by a small gap from its Luer-tapered section 26 and extending along this tapered section by a short distance from the rear end. The peg 27 is aligned with respect to the hub 21 and inner needle 20 such that, when the peg is engaged in the slot 18, the plane of the inclined tip 22 of the inner needle 20 lies approximately at right angles to the plane of inclined tip 12 of the outer needle 10.

At its rear end the hub 21 has a short slot 28 in its outer surface, that opens at the rear end of the hub and the purpose of which will become apparent.

Figure 4:
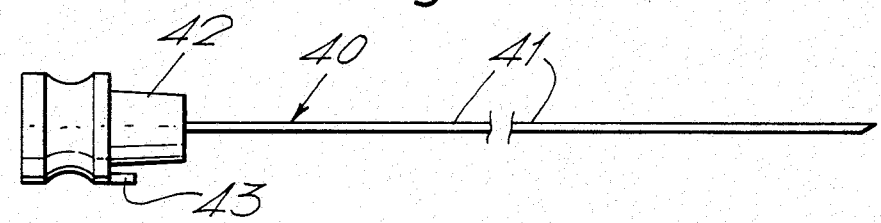
FIG. 4 shows a component used with the instrument.

In order to prevent body tissue entering the bore of either needle 10 or 20 during penetration, blocking rods are inserted through the bores of the needle to close their forward ends 12 and 22. One such blocking rod 40, for the outer needle assembly 1, is shown in FIG. 4. The blocking rod 40 comprises a solid plastics shaft 41 joined at its rear end with a plastics hub 42 by which the blocking rod is gripped. The length of the shaft 41 is such that when the assembly 40 is inserted in the outer needle 10, the tip of the shaft 41 lies flush with the inclined forward end 12 of the outer needle. In this respect, the forward end of the plastic shaft 41 is also inclined parallel with that of the outer needle 10. The hub 42 has an axial projection 43 that locates within the slot 18 in the hub 11 of the outer needle assembly 1 so as to ensure correct orientation of the inclined ends of the outer needle 10 and blocking rod 40. The other blocking rod 50 (see FIG. 7) used with the inner needle assembly 2 is of similar form except as regards its dimensions. The inner blocking rod 50 has an axial projection on its rear hub that engages the slot 28 in the hub 21 of the inner needle assembly.

Figure 5:
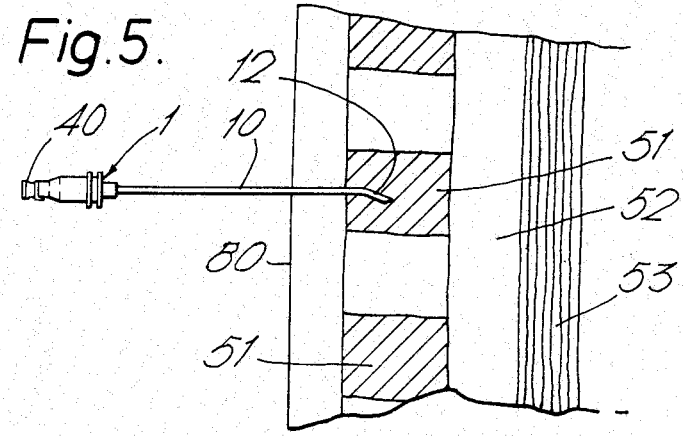
FIGS. 5 to 11 illustrate the instrument in use.
Figure 6:
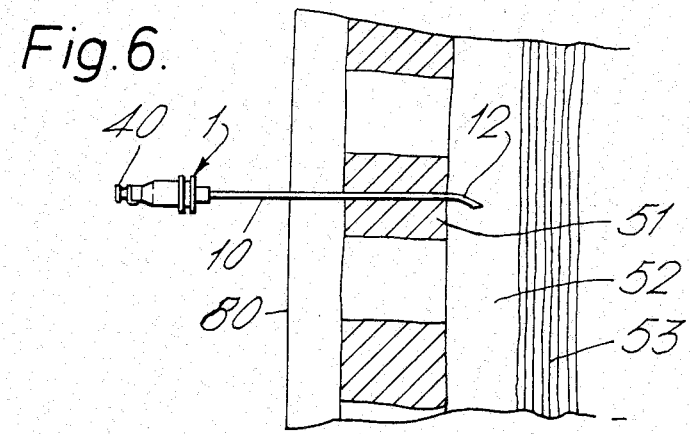

The use of the instrument will now be described with reference to FIGS. 5 to 11. First, as shown in FIG. 5 the outer Tuohy needle assembly 1, with its blocking rod 40 in place, is pushed forwardly perpendicularly through the patient's skin 80 and underlying tissue, with the bent tip 12 of the needle 10 directed generally caudad. The tip 12 of the needle 10 then passes into the spinal ligaments 51 which are of a dense, gristly nature, the presence of which is readily apparent to the surgeon by the increased resistance to penetration. As the needle assembly 1 is pushed further forwards, the tip 12 of the needle emerges from the spinal ligaments 51 into the epidural space 52. The presence of the epidural space 52 may be detected in various ways, such as, for example, as described in Patent Application No. GB 2083364A, or by simple observation of the distance of penetration. When this has occurred, as shown in FIG. 6, the blocking rod assembly 40 is removed and the inner, spinal needle assembly 2 is inserted with its blocking rod 50, through the outer needle assembly 1.

Figure 7:
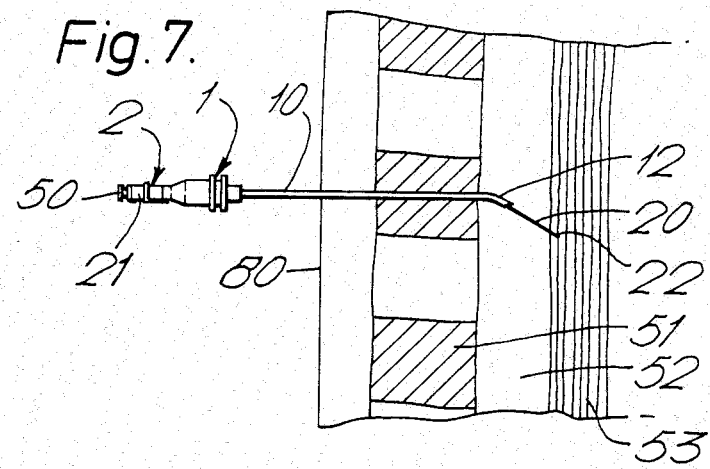
Figure 8:
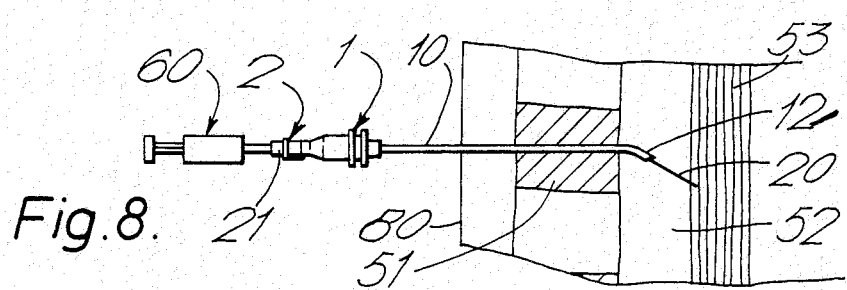
Figure 9:
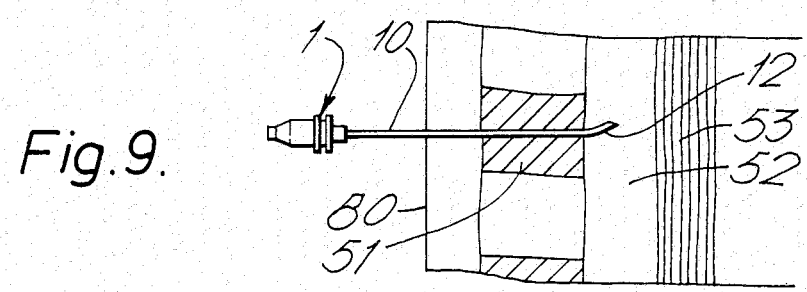
Figure 10:
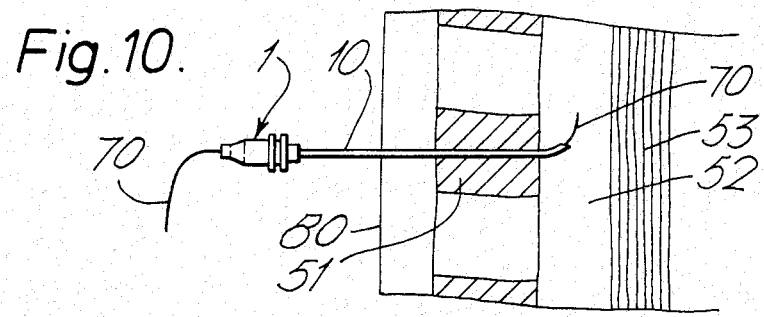

The inner needle 20 is sufficiently flexible to pass around the bend at the tip 12 of the outer needle 10 so that it emerges at an angle of about 20° to the horizontal. The locating peg 27 and slot 18 ensure that the inclined tip 22 of the spinal, inner needle 20 lies in a substantially vertical plane. Thus, since the filaments of the dura 53 extend substantially vertically, as the inner needle 20 is pushed further forwards, the dura is penetrated with the cutting edge 22 of the needle substantially parallel with the dura filaments (FIG. 7). In this way, damage to the dura is reduced and discomfort of the patient is minimized.

When the spinal inner needle assembly 2 is in position, having penetrated the dura 53, the blocking rod 50 is removed. If the instrument has been correctly located, cerebro-spinal fluid will flow along the bore of the needle 20 and into the hub 21. The transparent nature of the hub 21 enables the presence of the cerebro-spinal fluid to be readily observed before any significant quantities are lost. The tip of a syringe 60 is then inserted into the female Luer-tapered opening 25 (FIG. 8), and the required quantity of anaesthetic agent injected via the inner needle assembly 2 into the dura 53.

Figure 11:
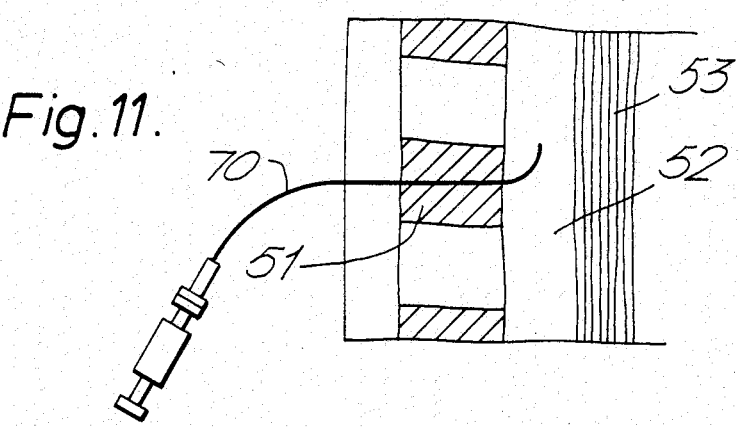

The inner needle assembly 2 is then withdrawn and the outer Tuohy needle assembly 1 is rotated through 180° (FIG. 9) so that its tip 12 is no longer aligned with the site on the dura 53 through which the inner needle 20 penetrated. An epidural catheter 70 (FIG. 10) is inserted through the outer Tuohy needle 10 so that it emerges into the epidural space 52, and the Tuohy needle is withdrawn to leave the catheter in position. Epidural anaesthesia is then carried out in the normal way by injection of an anaesthetic agent via the catheter 70 (FIG. 11).

What I claim is:

1. A medico-surgical instrument for use in epidural and spinal anaesthesia comprising: an outer hollow needle assembly having a hollow outer needle the forward end of which is bent away from the longitudinal axis of the instrument and has an inclined pointed tip, and a hub mounted at the rear of said outer needle, said hub having an engagement member provided therewith; and an inner hollow needle assembly having a hollow inner needle the forward end of which has an inclined pointed tip, and a hub mounted at the rear of said inner needle, the said hub of said inner assembly having an engagement member provided therewith that cooperates with the engagement member of the hub of said outer assembly so as to define a predetermined relative angular orientation between the inner and outer needle assemblies, the length of the inner needle being such that it projects beyond the forward end of the outer needle when said engagement members are in cooperation, and the relative angular orientation of the outer and inner needle assemblies being such that the plane of the inclined pointed tip of the inner needle is substantially at right angles with plane of the inclined pointed tip of the outer needle.

2. A medico-surgical instrument according to claim 1, wherein the forward end of said outer needle assembly is bent at an angle $\alpha$ of substantially 20° from the longitudinal axis of the instrument.

3. A medico-surgical instrument according to claim 1, wherein said engagement members are provided by a key and a keyway.

4. A medico-surgical instrument according to claim 1, wherein said engagement members are provided on the outer surfaces of the inner and outer needle assemblies.

5. A medico-surgical instrument according to claim 1, wherein the said pointed tip of the outer needle assembly makes an angle $\theta$ of substantially 10° with the longitudinal axis of the instrument.

6. A medico-surgical instrument according to claim 1, wherein the said pointed tip of the inner needle assembly makes an angle $\gamma$ of about 30° with the longitudinal axis of the instrument.

7. A medico-surgical instrument according to claim 1 wherein the said hub at the rear end of said inner needle assembly is fabricated of a transparent material through which fluid flowing through the inner needle assembly can be observed.

8. A medico-surgical instrument according to claim 1 wherein the said hubs at the rear ends of said inner and outer needle assemblies are each provided with a cooperating luer tapered surface.

9. A method of performing epidural and spinal anaesthesia using a medico-surgical instrument having an outer hollow needle assembly and an inner hollow needle assembly, each said assembly having an inclined pointed tip and a rear end, said inner needle assembly being slidable coaxially within said outer needle assembly, the said rear ends of the inner and outer needle assemblies being provided with cooperating engagement members that are locateable with one another to define a predetermined relative angular orientation between the inner and outer needle assemblies, the lengths of the inner and outer needle assemblies being such that the forward end of the inner needle assembly projects from the forward end of the outer needle assembly when the engagement members are located with one another, the method comprising the steps of: inserting the tip of said outer needle assembly into the epidural space of a patient; inserting said inner needle assembly through said outer needle assembly such that the tip of the inner needle assembly penetrates the dura of the patient, the cooperating engagement members and the pointed tip of the inner needle assembly being oriented such that the plane of the tip of the inner needle assembly is substantially parallel with the filaments of the dura; administering an anaesthetic agent via said inner needle assembly into the dura; removing said inner needle assembly; and administering an anaesthetic agent to the epidural space.

10. A method according to claim 9, including the step of rotating said outer needle assembly out of alignment with the site of penetration of the dura by the inner needle assembly, after removal of said inner needle assembly and prior to administration of the anaesthetic agent to the epidural space.

11. A method according to claim 9, including the steps of inserting a flexible catheter into the epidural space via said outer needle assembly after removal of said inner needle assembly, removing said outer needle assembly to leave said catheter in position, and administering the anaesthetic agent to the epidural space via said catheter.

12. A method according to claim 9, including the step of using a blocking rod to prevent body tissue entering said instrument during insertion.

* * * * *